US008909491B2

(12) United States Patent
Park et al.

(10) Patent No.: US 8,909,491 B2
(45) Date of Patent: Dec. 9, 2014

(54) MULTI-POINT INTERFEROMETRIC PHASE CHANGE DETECTION METHOD

(75) Inventors: Yeonjoon Park, Yorktown, VA (US); Sang Hyouk Choi, Poquoson, VA (US)

(73) Assignee: The United States of America as represented by the Adminstrator of the National Aeronautics and Space Adminstration, Washington, DC (US)

(*) Notice: Subject to any disclaimer, the term of this patent is extended or adjusted under 35 U.S.C. 154(b) by 540 days.

(21) Appl. No.: 13/411,891

(22) Filed: Mar. 5, 2012

(65) Prior Publication Data

US 2012/0224185 A1 Sep. 6, 2012

Related U.S. Application Data

(60) Provisional application No. 61/449,132, filed on Mar. 4, 2011.

(51) Int. Cl.
*G06F 19/00* (2011.01)
*G01N 21/45* (2006.01)
*G01B 9/02* (2006.01)

(52) U.S. Cl.
CPC ............ *G01N 21/45* (2013.01); *G01B 9/02083* (2013.01)
USPC .......................................................... 702/64

(58) Field of Classification Search
CPC .................... G02B 2027/0178; G02B 27/017; G06F 3/013; G06F 3/005; G06F 3/011
USPC ....................................... 702/64, 66, 182–185
See application file for complete search history.

(56) References Cited

U.S. PATENT DOCUMENTS

| 6,128,081 A | 10/2000 | White et al. |
| 7,324,214 B2 * | 1/2008 | De Groot et al. ............. 356/511 |
| 2006/0181714 A1 | 8/2006 | Mater et al. |

FOREIGN PATENT DOCUMENTS

WO 0104569 A1 1/2001

OTHER PUBLICATIONS

Yeonjoon Park, Sangjoon Park, Uhn Lee, Kunik Lee, Sang Choi, "Versatile Smart Optical Material Characterization System", Nanosensors, Biosensors, and Info-Tech Sensors and Systems 2010, edited by Vijay K. Varadan, Proc. of SPIE vol. 7646, 764613, 2010 SPIE.
Rene M. de Ridder, Alfred Driessen, Erwin Rikkers, Paul V. Lambeck Mart B.J. Diemeer, "Design and fabrication of electro-optic polymer modulators and switches". Optical Materials 12 (1999) 205-214.

(Continued)

*Primary Examiner* — Edward Raymond
(74) *Attorney, Agent, or Firm* — Jennifer L. Riley; Thomas K. McBride, Jr.

(57) ABSTRACT

Provided is a method for measuring multi-point interferometric angle changes beginning with an interferometric device capable of measuring at least one main point and at least one reference point. The method includes recording interferometric intensity changes on two or more spots using the main point and the reference point, and determining a sequence having a plurality of peak, local maximas and a plurality of valley, local minimas. The method includes sampling a first, partial sequence and comparing it to a neighboring, partial sequence using a perturbation analysis and additional calculation(s) to compile all phase angle changes for all measured points. Also provided is a computer implemented method to enable nanometer resolution sensitivity in a noisy signal and for characterization of a material in an interferometric device.

15 Claims, 6 Drawing Sheets

(56) References Cited

OTHER PUBLICATIONS

A. Balbin Villaverde, D. A. Donatti, D. G. Bozinis, "Terbium gallium garnet Verdet constant measurements with pulsed magnetic field", J. Phys. C: Solid State Phys., vol. 11, 1978. Printed in Great Britain 1978.

M.A. Jeppesen and A. M. Taylor, "Thickness and Refractive Index Measurement of a Lamina with a Michelson Interferometer", Journal of the Optical Society of America, vol. 56, No. 4, Apr. 1966.

* cited by examiner

US 8,909,491 B2

MULTI-POINT INTERFEROMETRIC PHASE CHANGE DETECTION METHOD

CROSS-REFERENCE TO RELATED APPLICATIONS

This patent application is related to copending U.S. patent application Ser. No. 12/964,381, filed Dec. 9, 2010. This patent application claims the benefit of U.S. Provisional Patent Application No. 61/449,132, filed Mar. 4, 2011.

STATEMENT REGARDING FEDERALLY SPONSORED RESEARCH AND DEVELOPMENT

The invention was made in part by employees of the United States Government and may be manufactured and used by or for the Government of the United States of America for governmental purposes without the payment of any royalties thereon or therefor.

BACKGROUND OF THE INVENTION

The interferometer is an instrument to make intensity change by the phase angle difference between two interfering coherent light beams. Two famous types of the interferometer are Michelson interferometer and Mach-Zehnder interferometer. Importantly, phase angle determination from the intensity change in the interferometer is an area that needs improvement. The bright spot and dark spot in the interferometer indicate in-phase and out-of-phase interference of two coherent beams. By counting the intensity maxima and minima during a movement, one can determine the displacement of a reflective object and measure the distance very accurately. Currently, several interferometric displacement sensors are commercialized in the market However, the conventional interferometric displacement sensors are designed for one or a few spot measurement only. Also, the conventional interferometric sensors are designed to measure the distance change only and are not designed to characterize an optical material inside a beam path. Accordingly, a need exists for expanding the measurement capability of an interferometer, which can improve its use for material characterization, among other activities.

BRIEF SUMMARY OF THE INVENTION

In at least one aspect, the invention provides a method for measuring multi-point interferometric angle changes beginning with an interferometric device capable of measuring at least one main point and at least one reference point. The method includes the steps of recording interferometric intensity changes on two or more spots using the main point and the reference point, and determining a sequence having a plurality of peak, local maximas and a plurality of valley, local minimas of intensities of the main point(s) and reference point(s). The method also includes sampling a first, partial sequence comprising a main peak, a main valley, a reference peak, and a reference valley, and comparing the first, partial sequence with a neighboring, partial sequence for each point of the sequence comprising at least a second main peak, a second main valley, a second reference peak, and a second reference valley. The method next determines a type of permutation of that neighbors each point as selected from the group consisting of ascending, descending, and transition permutations, and accordingly modifies a phase angle increment depending on the type of permutation for each point. The method also calculates phase angle changes of a plurality of intermediate points located between the main point(s) and the reference point(s) and compiles all phase angle changes for all measured points.

In another aspect, the invention provides a computer implemented method for measuring multi-point interferometric angle changes to enable nanometer resolution sensitivity in a noisy signal and for characterization of a material in an interferometric device capable of measuring at least one main point and at least one reference point. The method includes the step of recording interferometric intensity changes on two or more spots using the main point and the reference point. The method semi-automatically or automatically determines a sequence having a plurality of peak, local maximas and a plurality of valley, local minimas of intensities of the main point(s) and reference point(s). The method proceeds with the steps of sampling a first, partial sequence comprising a main peak, a main valley, a reference peak, and a reference valley; and comparing the first, partial sequence with a neighboring, partial sequence for each point of the sequence comprising at least a second main peak, a second main valley, a second reference peak, and a second reference valley. The method continues by determining a type of permutation of that neighbors each point as selected from the group consisting of ascending, descending, and transition permutations; and modifying a phase angle increment depending on the type of permutation for each point. The method calculates phase angle changes of a plurality of intermediate points located between the main point(s) and the reference point(s) using a sinusoidal interpolation; and makes a table of all phase angle changes for all points.

Additional objects, embodiments and details of this invention can be obtained from the following detailed description of the invention.

BRIEF DESCRIPTION OF THE SEVERAL VIEWS OF THE DRAWING(S)

FIG. 1 shows plots of intensity measurement and phase determination of (a) single main-point measurement, and (b) dual point (main+reference point) measurement. (c) Phase change determination with slope change is difficult when the real signal measurement in time domain contains a large noise. (d) Peak and valley position determination in the main and reference signals is relatively easy even in a large noise.

DETAILED DESCRIPTION OF THE INVENTION

The subject technology improves the functional capabilities of interferometers and interferometric devices. It allows the measurement of multiple phase angle changes. Traditionally interferometers are designed to take measurements at only one or a few spots. The instant invention allows measurement of multiple phase angles to enable nanometer resolution sensitivities in a noisy signal and for characterization of the material within the beam. An automated measurement system thus can gauge displacement, refractive index change, polarization change, magneto-optical property change, and other optical properties change(s), which thus expands the capabilities of interferometers, inter alia, in the material characterization industry.

Generally the phase angle of peaks (most constructive interference point, in-phase), and valleys (most destructive interference point, out-of-phase) are determined as prime phase angles, and intermediate points can be calculated, inter alia, as listed below, to get full phase angle data. Such full phase angle data can be used to calculate intrinsic and extrinsic properties of optical materials and devices such as refractive index change vs. voltages and so on.

Figures 1A, 1B, 1C, 1D:
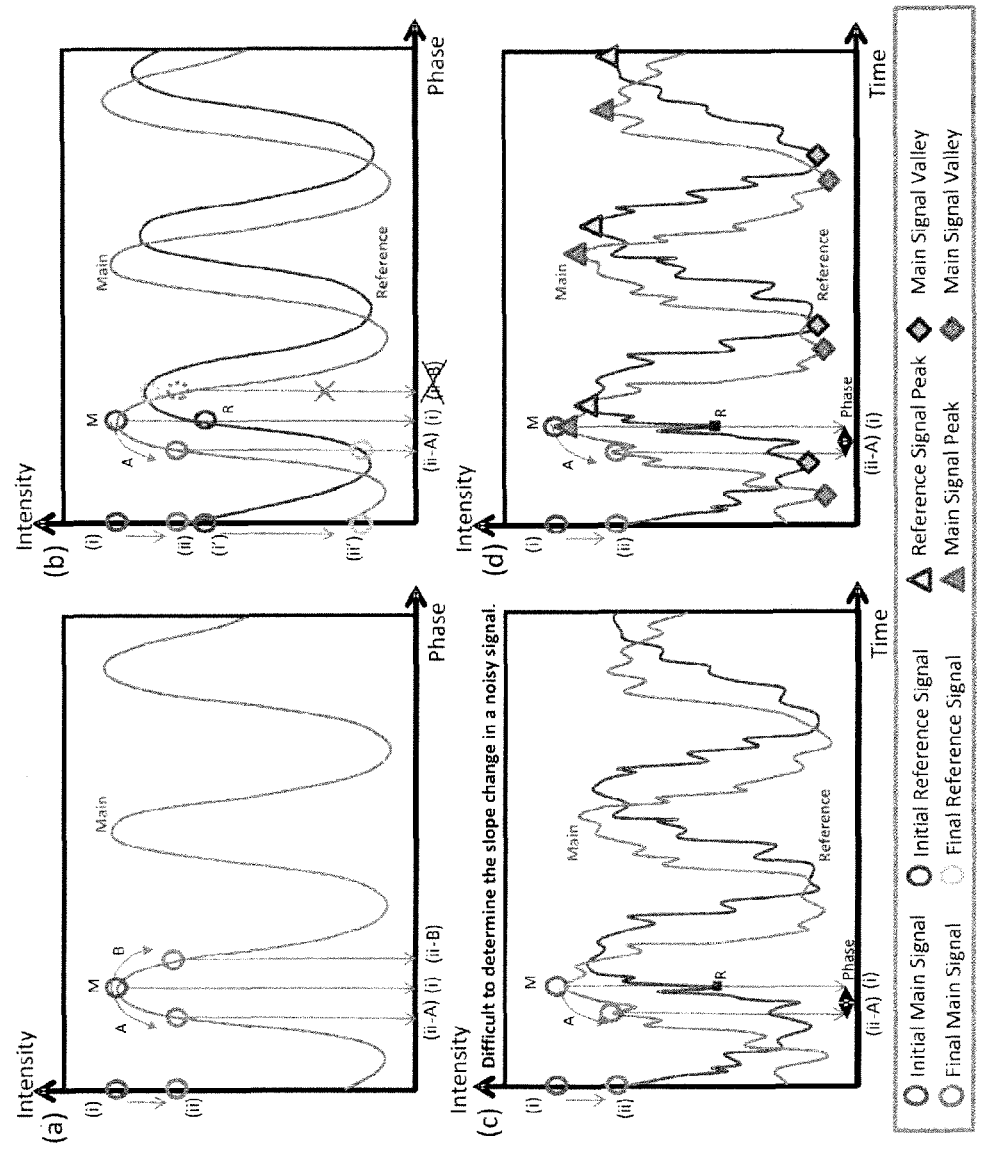

One can measure the intensity change of one point and find the phase angle changes by counting the intensity maxima and minima in the monotonously increasing or decreasing phase, but it is generally very difficult to measure an arbitrarily or a mixture of randomly increasing or decreasing phase angles. FIG. 1-(a) shows this problem of one point intensity measurement. When the initial intensity (i) changes the final intensity (ii) on Y-axis of FIG. 1-(a) graph: two cases, case A to phase (ii-A) and case B to phase (ii-B) on the X-axis of FIG. 1-(a) are possible. In this case, one cannot tell whether the phase angle is increasing to (ii-B) or decreasing to (ii-A) by observing the intensity change from (i) to (ii) alone.

If two points which have a phase relationship to each other can be measured simultaneously, the ambiguity of arbitrary phase determination can be removed. Suppose the intensities of a main point (M) and a reference point (R) are measured as shown in FIG. 1-(b). Then, the intensity of the main point changes from (i) to (ii) and that of the reference point changes from (i') to (ii'). By combining these two information, one can determine the phase changes from (i) to (ii-A) and not to (ii-B) as shown on the X-axis in FIG. 1-(b). Similarly, the first or the second derivative of reference point signal or main point signal can be used if two point-signals are well defined. However, in the actual measurement, the intensities of two-points are measured not in the phase unit but in the time unit and the noise are included as shown in FIG. 1-(c). The phase angle has to be calculated from the change of the intensity signals in time. Because determining the exact phase relationship of two signal intensities in a noisy situation is difficult, we invented a simple alternate method to calculate the phase angle of the main point signal by comparing the position the local maxima (peak) and minima (valley) of the main point and reference point as shown in FIG. 1-(d). The computer software collects the intensity data of at least two points, analyze, and determine the location the peaks (triangle marks) and valleys (diamond marks) of the main and reference signals.

Figure 2:
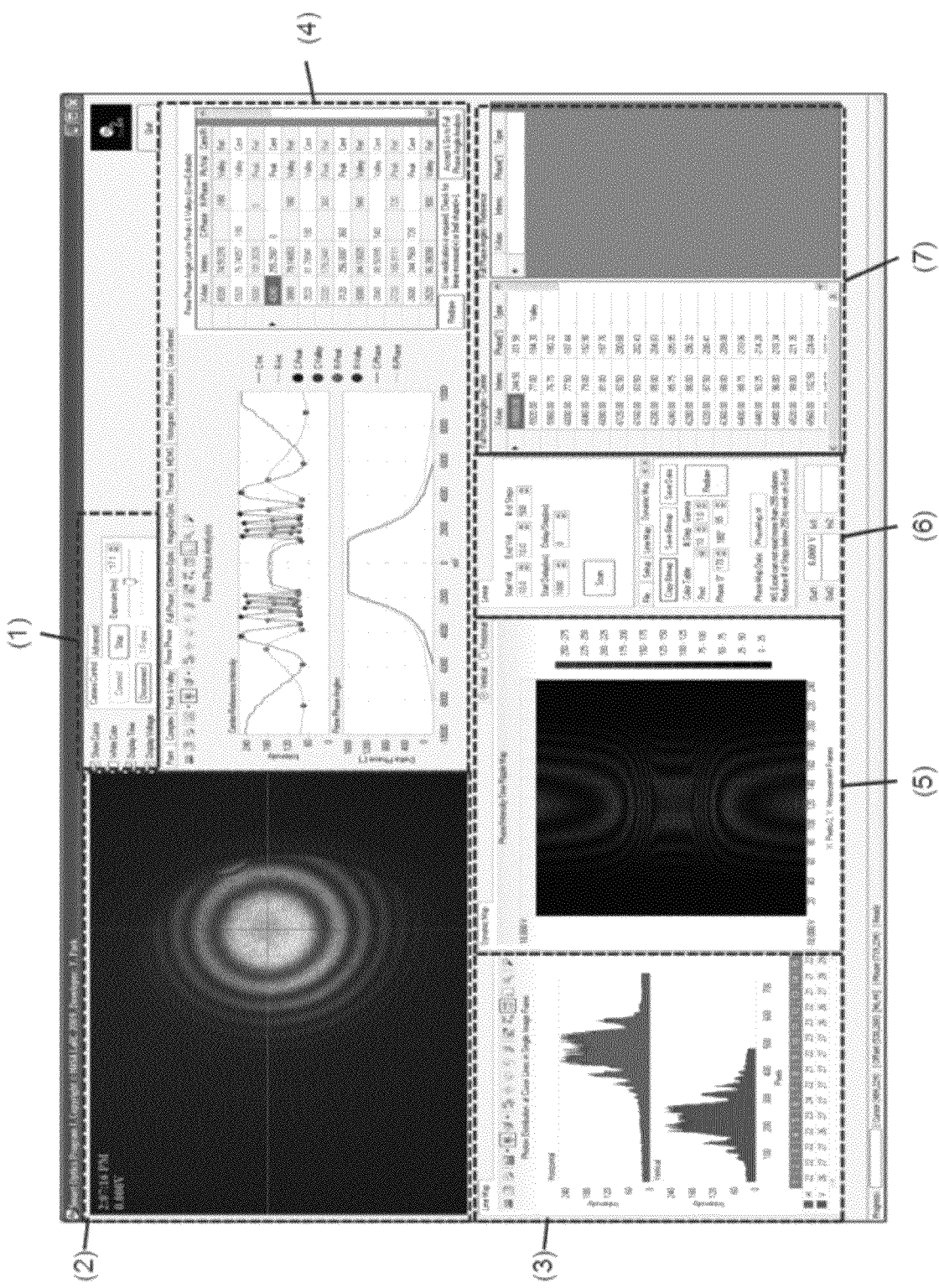
FIG. 2 shows a screenshot of an exemplary software interface for using at least one embodiment of the invention in an algorithm, the interface shown having seven sections.

The screenshot of exemplary developed software implementing at least one embodiment of the invention is shown in FIG. 2. The section (1) in FIG. 2 controls the imaging detector hardware. Section (2) is the real-time display of the detector image. The user defines the main point with a left mouse button click and the reference point with the right mouse button click. The main point appears at the junction of the two cross lines and the reference point appears at the corner of the surrounding rectangle. Two points are selected so that they are close to each other with in one phase cycle. Section (3) shows the real-time intensity plot along the two cross-lines, horizontal and vertical lines. Section (4) is the phase angle determination with automatic peak and valley detectors. Section (4) has multiple tab-windows for multi-analyses. Prime Phase tab is selected and it shows the prime phase angle change assignment to peaks and valleys. This section will be explained in detail later. Section (5) shows the time-evolution of interference intensities on the multi-pixels on the measurement axis. Section (6) is the measurement scan parameter setup window. Section (7) is the list of measured phase angle changes.

Figure 3:
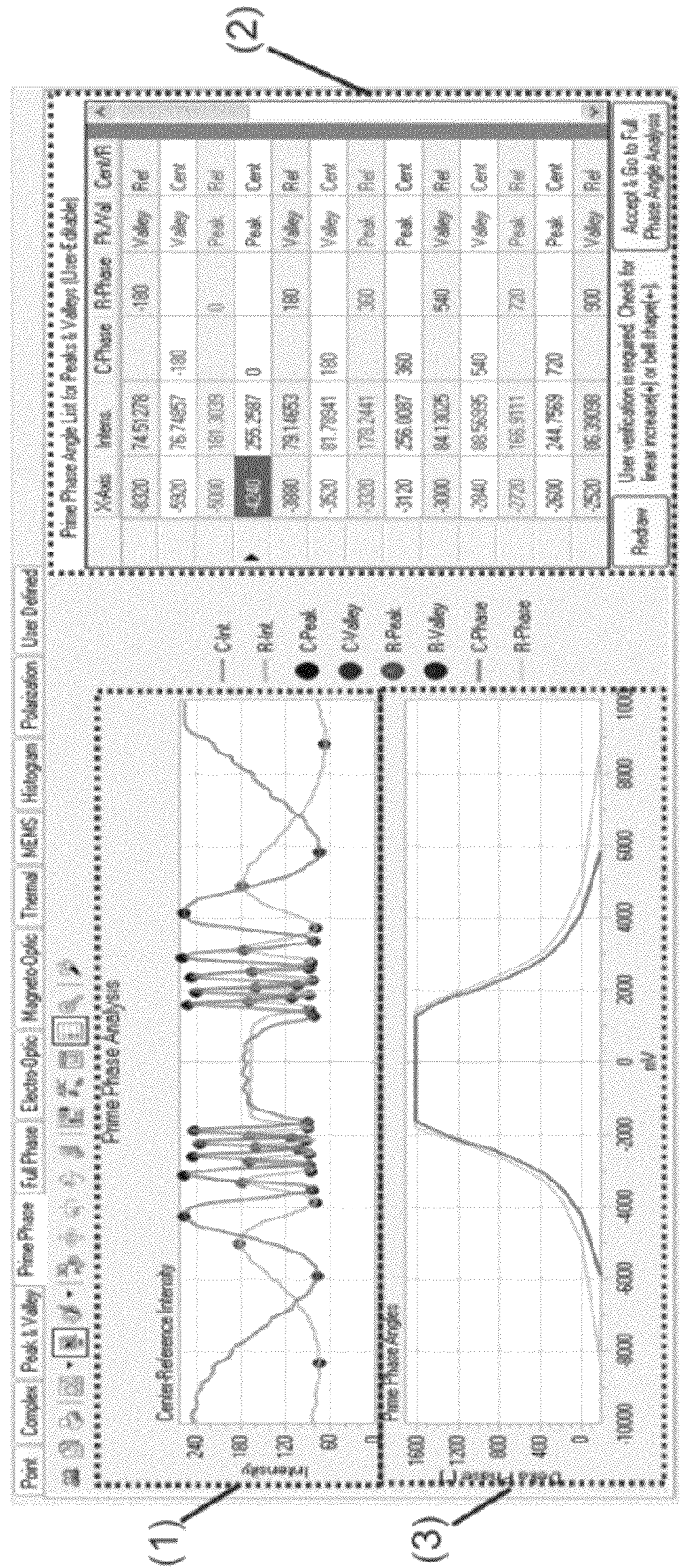
FIG. 3 shows a screenshot of a section of FIG. 2 with expanded details.
Figure 4:
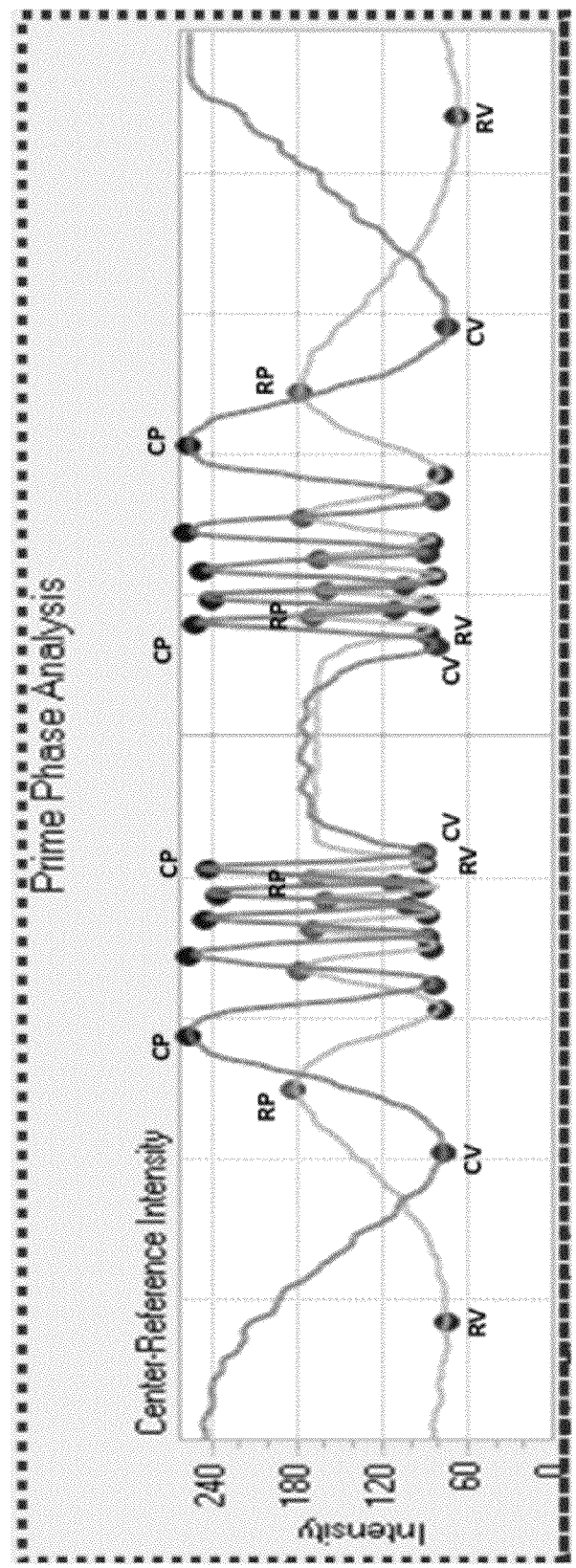
FIG. 4 shows a zoomed image of prime phase analysis peak assignments from FIG. 3.

The next FIG. 3 shows the zoomed image of section (4) in FIG. 2, the prime phase section. Section (1) in FIG. 3 shows the assignments of peak and valley positions of Main (Center) point and Reference point. The automatic peak detector picks up the positions of peaks and valleys with user programmable parameters. The blue line is for the Main (Center) point and the green line is for the Reference point. Once the user reviews and confirms the selected positions of peaks and valleys, the software automatically make a list and compares the locations of peaks and valleys of Main (Center) point with those of Reference point. The list of peak and valley positions is shown in Section (2). Based on this list, the software creates the order list of peaks and valleys of Main (Center) point and Reference point. The software creates string array with CP (Center Peak), CV (Center Valley), RP (Reference Peak), and RV (Reference Valley). For example, the graph in section (1) creates the following string array: RV, CV, RP, CP, RV, CV, RP, CP, RV, CV, RP, CP, . . . RV, CV, RP, CP, RV, CV, CV, RV, CP, RP, . . . CV, RV, CP, RP, CV, RV.

At a certain point, this order is reversed as . . . , RV, CV, CV, RV, . . . .

If we write this order list in different lower-case and capital letters.

RV, CV, RP, CP, RV, CV, RP, CP, RV, CV, RP, CP . . . RV, CV, RP, CP, RV, CV, cv, rv, cp, rp, . . . cv, rv, cp, rp, cv, rv.

The capital letter regions show the increase of phase angles and the lower-case letters region shows the opposite. Therefore we can easily see the cardinal order of the peaks and valleys of center and reference is reversed when the increase of phase angle is changed to the decrease of the phase angle. In order to use this cardinal order comparison to determine the absolute change direction of phase angles, it is necessary to compare all possible sets of "RV, CV, RP, CP". The measurement can start with "RV, CV, RP, CP" but also it can start with "CV, RP, CP, RV", "RP, CP, RV, CV", or "CP, RV, CV, RP". These four sets of the elements are called a permutation. For example, a permutation of "ABCD" is "BCDA", "CDAB", and "DABC". They are equal to "ABCD" and will be called the ascending permutation of "ABCD". The opposite descending permutation of "ABCD" is "dcba", which is the same as "cbad", "cdab", and "dabc". The software detects the permutation type whether it is ascending or descending and assigns the positive or negative phase angle changes. If the permutation is neither of ascending or descending permutation, the software reports an error in the measurement because the phase angle change cannot be determined. In the previous example, the elements can be rewritten as follows:

{ . . . RV, CV}, {RP, CP, RV, CV}, {RP, CP, RV, CV}, {RP, CP, . . . RV, CV}, {RP, CP, RV, CV}, {ey, rv, cp, rp}, . . . {cv, rv, cp, rp}, {cv, rv . . . }={ . . . C, D}, {A, B, C, D}, {A, B, C, D}, {B, . . . C, D}, {A, B, C, D}, {d, c, b, a}, . . . {d, c, b, a}, {d, c . . . }.

Therefore, this cardinal order determination using permutations of peaks and valleys of Main (Center) point and Reference point detects the absolute phase angle increase and decrease. When the interference maxima and minima occurs every $\Delta\theta$ angle, such as 360 degree, every group of ascending permutation adds $+\Delta\theta$ angle and every group of descending permutation adds $-\Delta\theta$ angle. Also, the phase angle does not change between the last D of {A, B, C, D} and the first D of {d, c, b, a} in the critically changing situation, . . . {A, B, C, D}, {d, c, b, a} . . . The experiment configuration determines $\Delta\theta$ angle, such as +360 degree or −360 degree for transmission (single pass through media) and +180 degree or −180 degree for reflection (double pass through media) and so on.

Section (3) shows the total prime phase angle changes, which changes from −180 degree to +1600 degree then comes back to −180 degree. The dark line is for the Main (Center) point and the light line is for the Reference point. This phase angle changes were actually measured with a liquid crystal layer under electric voltage. The X-axis shows the applied voltage in milli-Volt unit. The liquid crystal responds to the applied voltage symmetrically between (−) and (+) volt.

After these prime phase angles are determined for the peaks and valleys, the phase angles for the intermediate points between the peak and valley are easily calculated. For example, if the first peak with intensity P is at $\theta_1$ degree and the next valley with intensity V is at $\theta_1+180$ degree, the general phase angle, $\theta$ of the intermediate point with an intensity $I(\theta)$ is calculated by the following equations.

$$I(\theta) = \left(\frac{P-V}{2}\right)\cdot\cos(\theta-\theta_1) + \left(\frac{P+V}{2}\right) \quad \text{Eq. (1)}$$

$$\therefore \theta = \theta_1 + \arccos\left(\frac{2\cdot I - (P+V)}{P-V}\right), \quad \text{Eq. (2)}$$

where $$\theta_1 < \theta < \theta_1 + 180°$$

Figure 5:
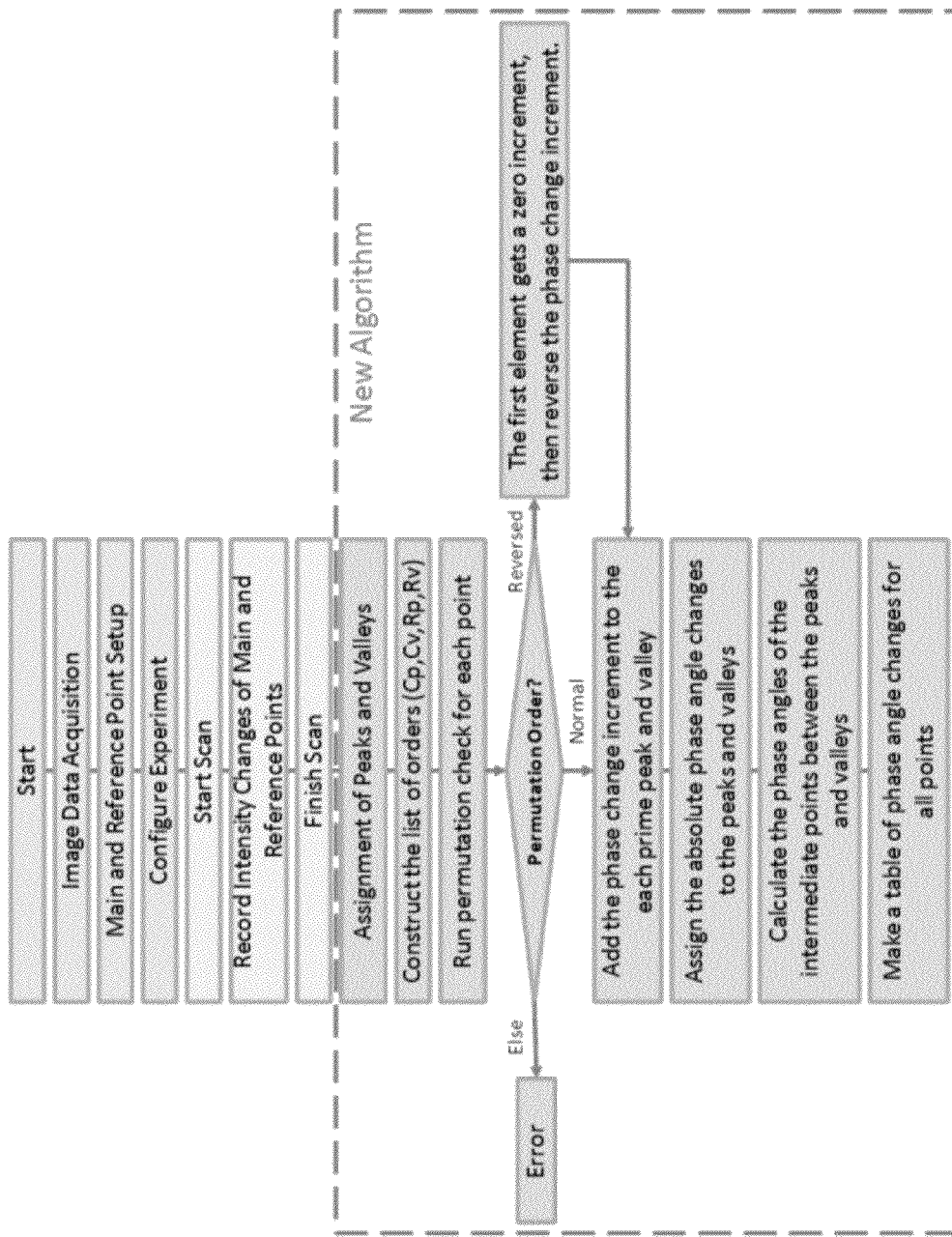
FIG. 5 shows a flow chart of a phase detection method in one embodiment that is based on a permutation type check for peaks and valleys of main and reference points.

FIG. 5 shows a flow chart for the phase angle change detection method, with at least one new algorithm shown inside the dashed box area. The first four boxes or steps in FIG. 5 are the initial setup for the measurement and the next three boxes or steps are the actual intensity measurement while applying the physical quantities such as voltage in time. The rest of the boxes, inside the larger dashed box, represent steps reflecting at least one embodiment of the invention as a new computer implemented algorithm to determine the phase angle changes. The peaks and valleys of the main (center) and reference points are determined by automatic, semi-automatic, or manual procedures. Then, the computer software constructs the list of orders for Center Peak (Cp), Center Valley (Cv), Reference Peak (Rp), and Reference Valley (Rv). Then, the software samples the first four elements and determines the permutation type, i.e. the sequence of Cp, Rp, Cv, and Rv. After the initial sampling, the computer checks the sequence of the next four elements group which starts at every element. If the sequence is the same (ascending) permutation type as the first four elements, it adds the fixed phase angle increment to the peak and valley points. If the sequence is the opposite, i.e. the descending permutation, it adds zero increment for the repeated peak or valley, then it subtracts the phase angle increment for the following negative permutation points. If the permutation of the points is not in ascending or descending order, the software generates an error message and stops converting the phase angle changes.

In this way, all the prime points, the peaks and valleys of the main and reference points can be assigned with the absolute phase angle changes. Once the phase angles of prime points are determined, the intermediate points between prime points are interpolated with sinusoidal interpolation equations like, inter alia, Eq. (1) and Eq. (2) shown above.

Therefore, the software determines the absolute phase angle changes of all points and creates a table or list of the phase angles for all measurement points. This information can be used for numerous scientific applications. For example, if the sample is a liquid crystal layer under the electric field, the X-axis is the applied voltage or E-field strength and Y-axis is the absolute phase angle changes. This graph gives how much changes would occur in the refractive index of liquid crystal layer under the voltage.

Also, the phase angle change measurement can be applied for magneto-optic materials, thermal expansion coefficient determination, electro-optic crystals and polymers, non-linear optical materials, polarization sensitive materials, and so on. For more details on a Smart Optical Characterization System and Method that can use many, if not all, aspects of the inventive methods disclosed herein, please see, for instance. U.S. patent application Ser. No. 12/964,381, filed Dec. 9, 2010, and Park et al., Versatile Smart Optical Material Characterization System, SPIE Conference—Smart Structures & Materials/NDE 2010, both of which are incorporated herein by reference thereto.

Figure 6:
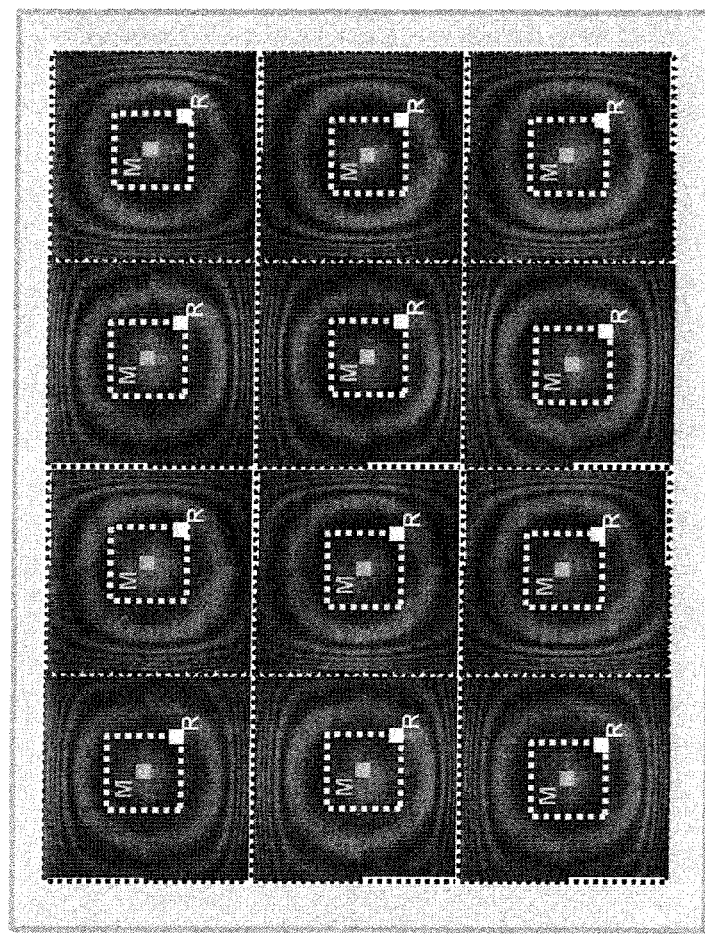
FIG. 6 shows an application of an embodiment of the phase angle determination method as it is applied to multiple pixels.

The above algorithm can be applied to multiple spots as well. FIG. 6 shows the application of the phase angle change determination algorithm to multiple pixels with the main point (M) and reference point (R). A single point or a few selected points can be used as the global phase reference point as well.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for measuring multi-point interferometric angle changes comprising the steps of:

(a) providing an interferometric device capable of measuring at least one main point and at least one reference point;
(b) recording interferometric intensity changes on two or more spots using the main point and the reference point;
(c) determining a sequence comprising a plurality of peak, local maximas and a plurality of valley, local minimas of intensities of the main point(s) and reference point(s);
(d) sampling a first, partial sequence comprising a main peak, a main valley, a reference peak, and a reference valley;
(e) comparing the first, partial sequence with a neighboring, partial sequence for each point of the sequence comprising at least a second main peak, a second main valley, a second reference peak, and a second reference valley;
(f) determining a type of permutation of that neighbors each point as selected from the group consisting of ascending, descending, and transition permutations;
(g) modifying a phase angle increment depending on the type of permutation for each point;
(h) calculating phase angle changes of a plurality of intermediate points located between the main point(s) and the reference point(s); and
(i) compiling all phase angle changes for all measured points.

2. The method of claim 1, wherein the step of recording the intensity changes further comprises the step of applying physical quantities over time to a sample contained in the device.

3. The method of claim 2, wherein at least one physical quantity applied comprises voltage.

4. The method of claim 1, wherein step (c) of determining is selected from the group consisting of automatic, semi-automatic, and manual determination procedures.

5. The method of claim 1, wherein step (h) comprises using a sinusoidal interpolation.

6. The method of claim 1, wherein step (g) comprises adding or subtracting a phase angle increment.

7. The method of claim 1, wherein step (g) comprises keeping a constant value for a permutation type that is not ascending nor descending.

8. The method of claim 1, wherein the method is applied to multiple pixels with an individual main point and an individual reference point in each pixel.

9. The method of claim 1, wherein the method is applied to multiple pixels with an individual main point in each pixel and a single or a few points as the global phase reference point.

10. The method of claim 1, wherein step (i) further comprises making a table of phase angle changes for all points.

11. A computer implemented method for measuring multi-point interferometric angle changes to enable nanometer resolution sensitivity in a noisy signal and for characterization of a material in an interferometric device capable of measuring at least one main point and at least one reference point, said method comprising the steps of:

(a) recording interferometric intensity changes on two or more spots using the main point and the reference point;
(c) semi-automatically or automatically determining a sequence comprising a plurality of peak, local maximas and a plurality of valley, local minimas of intensities of the main point(s) and reference point(s);
(d) sampling a first, partial sequence comprising a main peak, a main valley, a reference peak, and a reference valley;
(e) comparing the first, partial sequence with a neighboring, partial sequence for each point of the sequence comprising at least a second main peak, a second main valley, a second reference peak, and a second reference valley;
(f) determining a type of permutation of that neighbors each point as selected from the group consisting of ascending, descending, and transition permutations;
(g) modifying a phase angle increment depending on the type of permutation for each point;
(h) calculating phase angle changes of a plurality of intermediate points located between the main point(s) and the reference point(s) using a sinusoidal interpolation; and
(i) making a table of all phase angle changes for all points.

12. The method of claim 11, wherein step (g) comprises adding or subtracting a phase angle increment.

13. The method of claim 11, wherein step (g) comprises keeping a constant value for a permutation type that is not ascending nor descending.

14. The method of claim 11, wherein the method is applied to multiple pixels with an individual main point and an individual reference point in each pixel.

15. The method of claim 11, wherein the method is applied to multiple pixels with an individual main point in each pixel and a single or a few points as the global phase reference point.

* * * * *